(12) United States Patent
Rosenbury (10) Patent No.: US 7,898,455 B2
(45) Date of Patent: Mar. 1, 2011

(54) HANDHELD INSTRUMENT CAPABLE OF MEASURING HEARTBEAT AND BREATHING MOTION AT A DISTANCE

(76) Inventor: Erwin T. Rosenbury, Castro Valley, CA (US)

( * ) Notice: Subject to any disclaimer, the term of this patent is extended or adjusted under 35 U.S.C. 154(b) by 753 days.

(21) Appl. No.: 11/778,697

(22) Filed: Jul. 17, 2007

(65) Prior Publication Data

US 2010/0026550 A1    Feb. 4, 2010

(51) Int. Cl.
*G01S 13/00* (2006.01)
(52) U.S. Cl. .......................................... 342/22
(58) Field of Classification Search ............... 342/22, 342/27, 28; 600/407
See application file for complete search history.

(56) References Cited

U.S. PATENT DOCUMENTS

| | | | |
|---|---|---|---|
| 7,148,836 B2* | 12/2006 | Romero et al. | 342/22 |
| 7,492,325 B1* | 2/2009 | Moosbrugger et al. | 342/373 |
| 7,567,200 B1* | 7/2009 | Osterweil | 342/28 |
| 2006/0028369 A1* | 2/2006 | Rausch et al. | 342/22 |
| 2006/0061504 A1* | 3/2006 | Leach et al. | 342/22 |
| 2006/0170584 A1* | 8/2006 | Romero et al. | 342/22 |
| 2008/0238757 A1* | 10/2008 | Lin et al. | 342/22 |
| 2010/0026550 A1* | 2/2010 | Rosenbury | 342/22 |

* cited by examiner

*Primary Examiner* — Dan Pihulic
(74) *Attorney, Agent, or Firm* — White-Welker & Welker, LLC (57) ABSTRACT

The apparatus of the present invention consists of a MicroPower Radar (MPR), a data acquisition (DAQ) element and a PDA. The radar sends a short, low-amplitude signal of radio-frequency (RF) energy toward the target scene. This signal reflects from the target and is received as a Doppler change. RF has the advantages of penetrating clothing while operating at one fiftieth the power of a cellular or cordless phone. This Doppler change in signal amplitude is filtered, amplified and presented to the DAQ. The DAQ converts the analog Doppler signal into a digital bit-stream and passed to the processor. Proprietary software analysis is performed to further filter and to make a Live/Dead determination. The radar antenna is located at the back of the device and should be pointed toward the victim, the display facing the operator.

20 Claims, 8 Drawing Sheets

HANDHELD INSTRUMENT CAPABLE OF MEASURING HEARTBEAT AND BREATHING MOTION AT A DISTANCE

FEDERALLY SPONSORED RESEARCH

Not Applicable

SEQUENCE LISTING OR PROGRAM

Not Applicable

CROSS REFERENCE TO RELATED APPLICATIONS

Not Applicable

TECHNICAL FIELD OF THE INVENTION

The present invention relates generally to radar systems. More specifically, the present invention relates to a hand-held micro powered radar for life detecting through Doppler measurement.

BACKGROUND OF THE INVENTION

The objective is to build a single-piece Rubble Rescue Radar (RRR) system. The system will combine inventor's proven radar with data acquisition, processing hardware and Inventor's algorithms and software. The combined system must be able to measure, detect, process and indicate real-time results.

Inventor currently produces handheld pre-production prototype radars for Government applications. Multiple versions of prototype radars have been built and demonstrated that meet all of the requirements for a rubble penetrating device. Inventor has unique impulse technology based on intellectual property, an advanced development (diverse engineering skills) capability, and practical experience integrating UWB systems.

Inventor is developing MicroPower Radars (MPR) for commercial and government applications including weapons diagnostics, covert military applications and other defense mission support. Inventor engineers can shape impulses to fit almost any application.

Inventor's MPR Systems are a fundamentally different type of wireless device. Based on new Inventor intellectual property, know-how, and expertise, inventor's sensors emit much shorter pulses than most radars and randomizes the timing of these pulses. Inventor has also developed ultra-wideband antennas, which are matched to the radar signal and has experience in optimizing antennas for different applications. These design advantages are discussed further below. Finally, because the MPR systems are built out of a small number of common electronic components, they are compact and inexpensive to produce. General specifications of inventor's typical existing systems is outlined below:

Based on emitting and detecting very low amplitude and short voltage impulses, the MPR has a very sensitive window for accurately detecting reflections from boundaries between different materials. Many of these radar systems can also be considered "digital," because they emit very fast edges of digital square waves and then upon receiving impulse signals, immediately convert back into digital signal. Sensors make up the majority of systems prototyped to date; however, communication devices have also been demonstrated.

Another approach in the design of RCLAD is to exploit signal-processing gain through spectral analysis for the detection of heartbeat and breathing. Note, that in the ROC curves presented above, multiple pulses can make a significant difference in detection. Spectral match filtering employs the entire radar return sequence (i.e. multiple arrivals or pulses). Detection in the spectral domain will therefore afford a processing gain of approximately 13 dB for a 20 second observation window, as the period of an heart beat is only about 1 sec. Should further investigation on the signal spectral analysis methods prove to be more successful, the radar pulse amplitude and antenna gain need not be increased significantly from inventor's present design.

As an example of signal processing, shown below is a simulation of the heart beat detection for multiple subjects with observation at 10 s and 5 s window length. As depicted by the spectral plots in FIG. 7, the two heartbeats are clear in the longer (top) observation window of 10 sec., but is lacking for the shorter observation window of 5 sec. (below).

Longer integration times (time-on-target) help to resolve individual targets. Inventor's radar will display prompt results that a target exists and the longer the radar remains on-target, the more resolution the radar will achieve. In addition, the confidence level of the estimate will increase with time on target. Results clearly indicate.

Inventor has developed a prototype that is able to discriminate between targets in order to permit casualty location. The handheld scanner shall provide a snapshot azimuth and range information for a minimum of forty yards open air, twenty feet through non-conducting obstructions such as rubble.

Inventor recently developed a flashlight-sized radar capable of detecting the heartbeat and breathing motion of human targets through foliage and light rubble. The extreme sensitivity to such small movements by such small targets comes at a price—platform stability. If the platform moves, the small target signal may be swamped by the signal generated by the platform motion. This analysis was designed to determine the tolerable platform motion. First the target signal will be evaluated then the platform motion signal (vs. amplitude and frequency) will be measured. From these, an estimate of motion tolerance may be derived.

SUMMARY OF THE INVENTION

The apparatus of the present invention consists of a MicroPower Radar (MPR), a data acquisition (DAQ) element and a PDA. The radar sends a short, low-amplitude signal of radio-frequency (RF) energy toward the target scene. This signal reflects from the target and is received as a Doppler change. The radar's RF energy is in the same band as many cordless phones and operates at much lower powers. RF has the advantages of penetrating clothing while operating at one fiftieth the power of a cellular or cordless phone. This Doppler change in signal amplitude is filtered, amplified and presented to the DAQ. The DAQ converts the analog Doppler signal into a digital bit-stream and passed to the processor. Proprietary software analysis is performed to further filter and to make a Live/Dead determination.

The radar antenna is located at the back of the device. This antenna should be pointed toward the victim (or test subject), the display facing the operator. The output signal is extremely small, less than one-fiftieth a cell phone's signal amplitude. The return signal is likewise, even smaller.

The present invention is intended to operate with the radar pointing toward the victim and the display pointed toward the operator. The display system elements include the processor/ display, control buttons and a data acquisition element. The antenna system contains the antenna and the radar.

The radar is the key technological breakthrough that enables the present invention operation. The radar is a pulse Doppler design with MTI (moving target indicator) and STC (sensitivity time control). The radar thereby creates a zone or bubble of detection. Any motion within the bubble results in an analog signal reported at the output of the radar. The system collects radar signal information and signal processing is used to calculate target parameters. A new data point is presented every second and data is used from the previous sixteen seconds to calculate target presence, confidence and rates.

It is therefore an objective of the present invention to teach a high reliability, low false alarm heartbeat/breathing detection apparatus. Such an apparatus should be able to detect heartbeat and breathing rates from a distance of forty feet through-wall, through-foliage, and through-clothing.

It is another objective of the present invention to teach a low radar power consumption equivalent to four double A batteries.

It is also an objective of the present invention to teach an apparatus with an antenna that separates from the display for remote operation.

It is still another objective to teach an apparatus with low noise receiver for sensitive detection, less than 1 micro-volt typical.

It is a final objective of the present invention to teach an apparatus that enables multi-target detection.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, functional, mechanical, electrical, and other changes may be made without departing from the scope of the present invention. The following detailed description is therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention.

The size of a handheld radar system is largely determined by the laws of physics (antenna, power), the diffraction limit and the batteries required to meet the range requirement. The remaining dimensions are defined by technology (processor, radar circuitry, etc.). The range of operational concrete penetrating frequencies that provide the possibility of meeting the forty foot to one hundred foot detection range are between six hundred MHz and three GHz corresponding to an antenna linear dimension of approximately eight inches on a side. Even if it were possible to trade transmit power for antenna size, increased battery size would be unacceptable, as would an increased antenna size. A balance of physical characteristics for a forty-foot to one hundred foot, 2.4 GHz radar therefore include, an eight inch on a side and multiple C or D-cell batteries.

The present invention is to develop radar sets for the purpose of detecting human heartbeat and breathing at forty-foot range. Initially the units are to be mounted on a stationary platform such as a tripod. Later the units are to be integrated with a gyroscopically stabilized platform which an operator might use to point the radar at a person to determine a live/dead condition and register pulse and respiration rates.

The present invention it was developed in several 'Builds' which iteratively develop the desired capability. The first build was for initial radar development, algorithm tuning, and operation using a stationary mounting. Later 'Builds' enhance capability for mobile operation and develop user interfaces.

The first build's development resulted in prototype radars configured for laboratory testing as described below, for the purpose of proving hardware and algorithm suitable to the objective. Testing identifies settings and operation conditions under which the units perform and their expected capability. Testing also identifies changes to accommodate requirements of following builds and operation conditions for those builds.

Testing conducted by the end of the first build confirmed the feasibility of the hardware and algorithms, and justify following Builds.

The goal of the present invention is to develop a handheld instrument capable of measuring heartbeat and breathing motion at a distance. The radar hardware was developed sufficient to the task, algorithms were developed to process the tiny signals, and handheld data acquisition and processor hardware was designed and fabricated.

Figure 6:
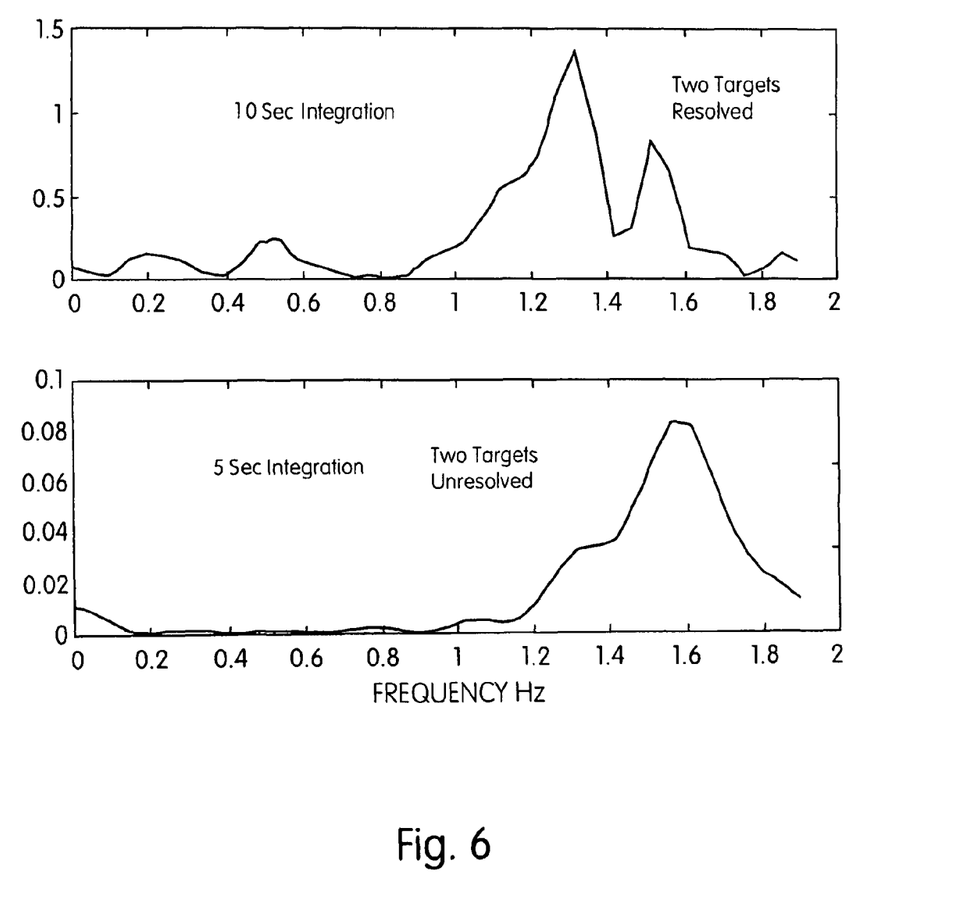
FIG. 6 illustrates that a ten second integration time (upper) resolves two living targets—while a five second integration time (lower) does not.

Test results, illustrated in FIG. 6, show that, in general, the platform must be stabilized to one micron. Platform motion was measured vs. radar signal output in a typical (lab) environment. The signal level was extrapolated to the minimum detectable signal and the minimum acceptable platform motion derived. Motion greater than one micron will interfere with the radar computer's ability to discriminate heart and breathing targets.

A number of items remain to increase the robustness of instrument operation: Integrate the Radar, DAQ, Processor and Software into a manufacturable handheld package, single board radar; an increase operator heartbeat isolation by sensing the operator's heart/breathing signal on a second channel and subtracting it in software, wooded & vegetated environments, heart signature processing; Clutter artifacts (e.g. blowing foliage) will be filtered and compensated for through algorithm developments; Compensate micro-motion (e.g. pulse) in the operator's hand by a mechanical feedback control to hold the antenna steady, 3-axis active control; Improved controls & displays, operator stability feedback [accelerometers], contact/history list, display visibility; and Optimize system power utilization, and improve processing of detected physiologic and biometric phenomena.

A number of items remain to increase the overall system capability by: increasing the standoff range from fifty feet to one hundred and twenty fee or twenty feet through obstructions; Side-to-side (azimuthal) target resolution by implementing a monopulse antenna, sum and difference circuitry, DAQ, processing and processing software; Operate as a tracker system; assess functionality, form/fit, and the potential for airworthiness; Integrate Marco Polo networking, databasing, and uplinking linked to the casualty tracker system; Provide the units for human factors evaluation; purchase, or design and build ETag components; Integrate ETag with scanner and/or the casualty tracker system; Support interoperability with Battlefield Airman equipment and ARMIS components; and Test and demonstration requirements.

Radar design of the present starts with the application, concept of operation, operational requirements, etc. Key considerations are size, weight, beam width, resolution, center frequency, bandwidth and often penetration depth. The main elements that make up a radar are the transmitter, antenna, receiver, processor*, display and power source (battery).

The first consideration is to perform a link margin calculation. Assuming the application is within reach, frequency selection is a primary consideration. Several factor go into frequency selection including regulatory (FCC) requirements, penetration etc. Frequency determines antenna size and leaves transmit power as the remaining factor.

An example might be a radar to determine battlefield remote casualty status including live-dead determination, heart rate and breathing status. With these data, a medic may determine risk/reward tradeoffs for rescue efforts.

Example requirements might include detection at 100', an FCC/NTIA/JSC requirement to operate at 2.4 GHz, a general handheld requirement (smaller is better) and a general desire to penetrate rubble/concrete.

Even though the frequency has been selected, a brief discussion of frequency/antenna selection is in order. Now referring to FIG. 7, Antenna size vs beam width and frequency implies that higher frequency is desirable.

Figure 7:
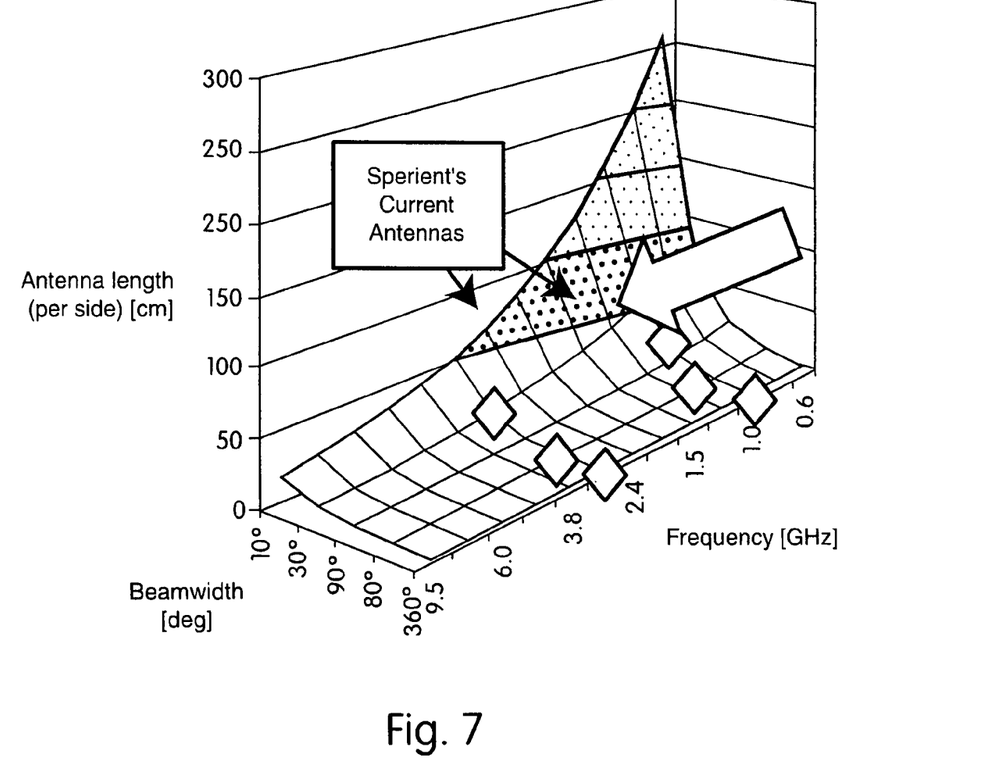
FIG. 7 is a chart illustrating Antenna size vs beam width and frequency implies that higher frequency is desirable.
Figure 8:
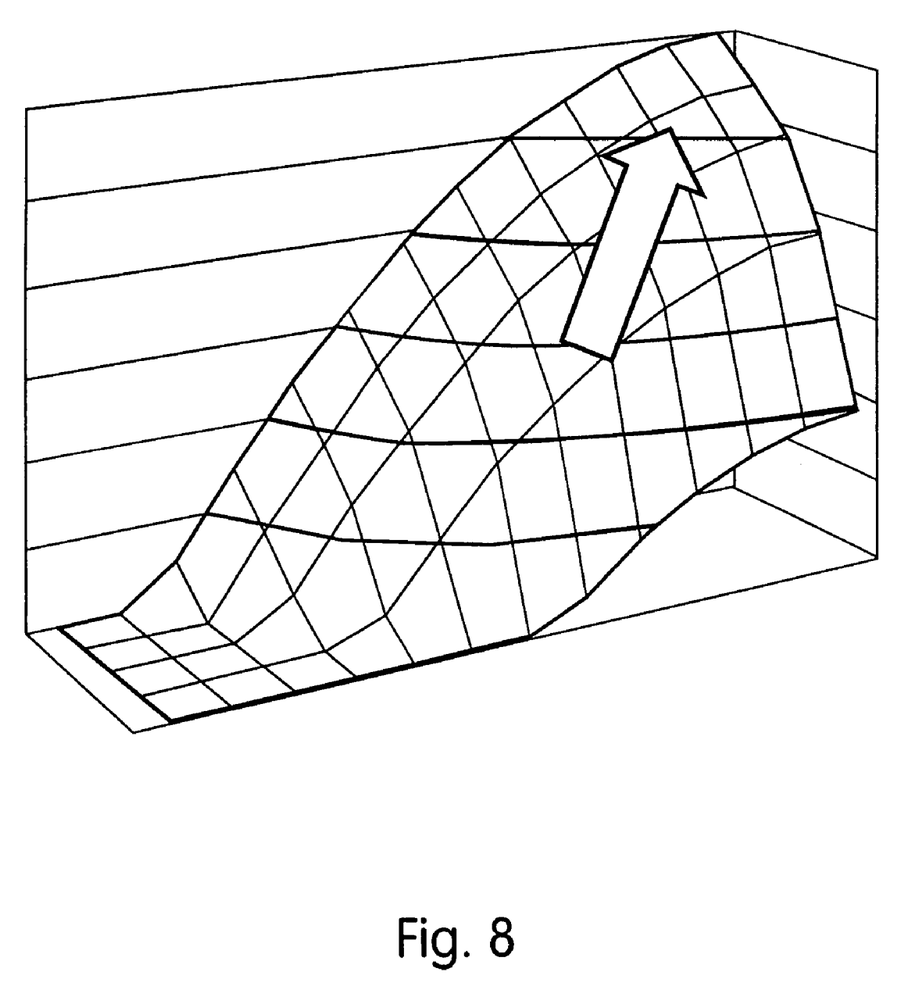
FIG. 8 is a chart illustrating relative signal strength vs frequency and concrete depth shows that lower frequencies (larger antennas) are desirable.

Conflicting requirements often arise from the fact that smaller beam widths are created by larger antennas. This is a fundamental law of physics (re: diffraction limit). A three dimensional plot describes the theoretical limits for antenna size vs frequency for various beam widths. Also plotted are some of Inventor's antenna implementations (hardware). Propagation loss drives the requirements in the opposite direction. Lower frequencies penetrate better and therefore, a balance of frequency; antenna size and beam width must be found. The importance of rubble/foliage penetration must be weighed against range performance. As shown in FIG. 8, Relative signal strength vs frequency and concrete depth shows that lower frequencies (larger antennas) are desirable.

The free parameter is power. Inventor designs some of the highest power (30 Watt) handheld amplifiers available. This level of power requires multiple D-cell batteries. Lower power systems are available with AA batteries, with associated reduction in range.

The major hardware elements have been selected (PDR draft selections subject to review). The major components consist of the radar (transmitter, receiver), data acquisition, display and power supply. The radar consists of several circuit boards mounted in a stack. The processor/DAQ consists of two circuit boards in a stack. The display is a 5.5-Inch LCD enabling vivid color display even in bright sunlight.

Figure 1:
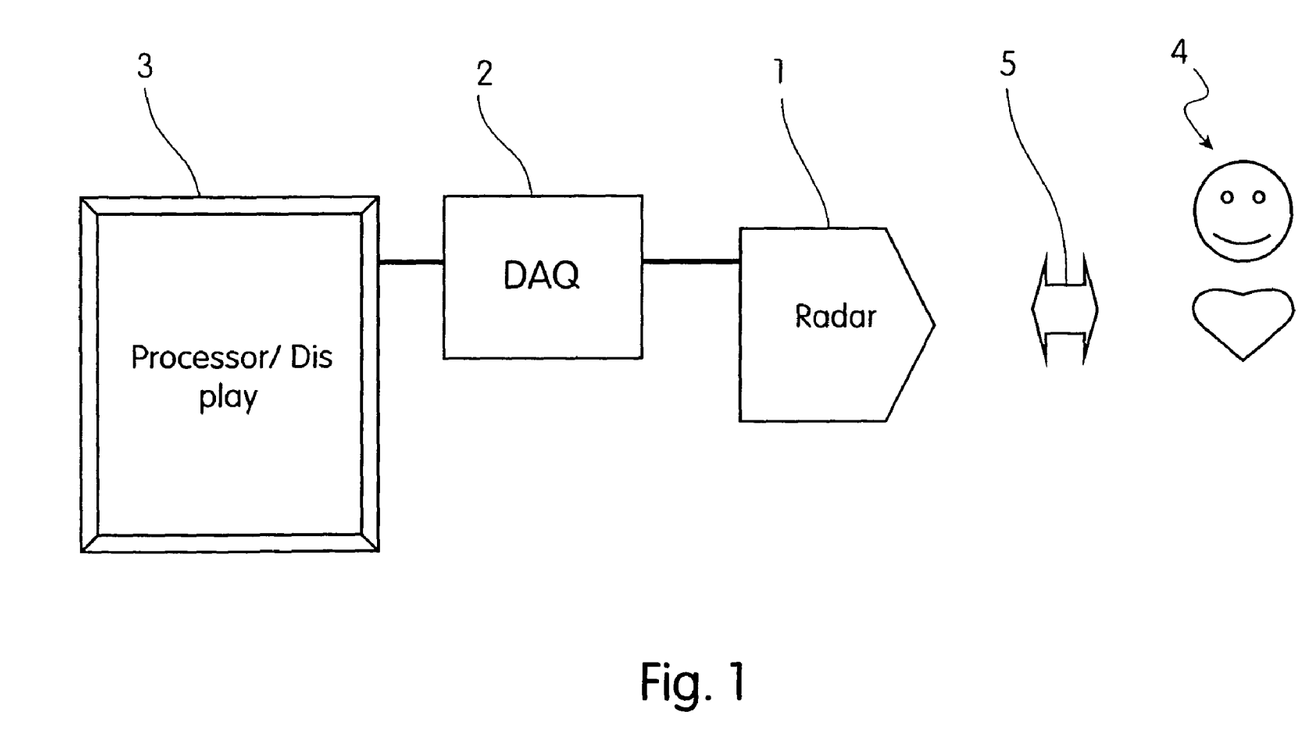
FIG. 1 is a block diagram of the powered radar of the present invention.

Now referring to FIG. 1, the system consists of a MicroPower Radar (MPR) 1, a data acquisition (DAQ) element 2 and a PDA 3. The MicroPower Radar (MPR) 1 sends a short, low-amplitude signal of radio frequency (RF) energy 5 toward the target scene 4. This signal reflects 5 from the target scene 4 and is received as a Doppler change.

The radar's RF energy 5 is in the same band as many cordless phones and operates at much lower powers. RF has the advantages of penetrating clothing while operating at one fiftieth the power of a cellular or cordless phone. This Doppler change in signal amplitude is filtered, amplified and presented to the DAQ 2. The DAQ 2 converts the analog Doppler signal into a digital bit-stream and passed to the processor 3. Proprietary software analysis is performed to further filter and to make a Live/Dead determination.

The radar antenna is located at the back of the device. This antenna should be pointed toward the victim or test subject, the display facing the operator. The output signal is extremely small, less than one-fiftieth a cell phone's signal amplitude. The return signal is likewise, even smaller.

The present invention is intended to operate with the radar pointing toward the victim and the display pointed toward the operator. The display system elements include the processor/display, control buttons and a data acquisition element. The antenna system contains the antenna and the radar.

The radar is the key technological breakthrough that enables the present invention operation. The radar is a pulse Doppler design with MTI (moving target indicator) and STC (sensitivity time control). The radar thereby creates a zone or bubble of detection. Any motion within the bubble results in an analog signal reported at the output of the radar. The system collects radar signal information and signal processing is used to calculate target parameters. A new data point is presented every second and data is used from the previous sixteen seconds to calculate target presence, confidence and rates.

The radar system of the present invention provides high reliability, low false alarm heartbeat/breathing detection for a distance of forty feet through-wall, through-foliage, and through clothing. The radar system provides low radar power consumption equivalent to four AA batteries and has an antenna that separates from the display for remote operation. Low noise receiver for sensitive detection of heartbeat and breathing rates of less than 1 microvolt and multi-target detection.

Figure 2:
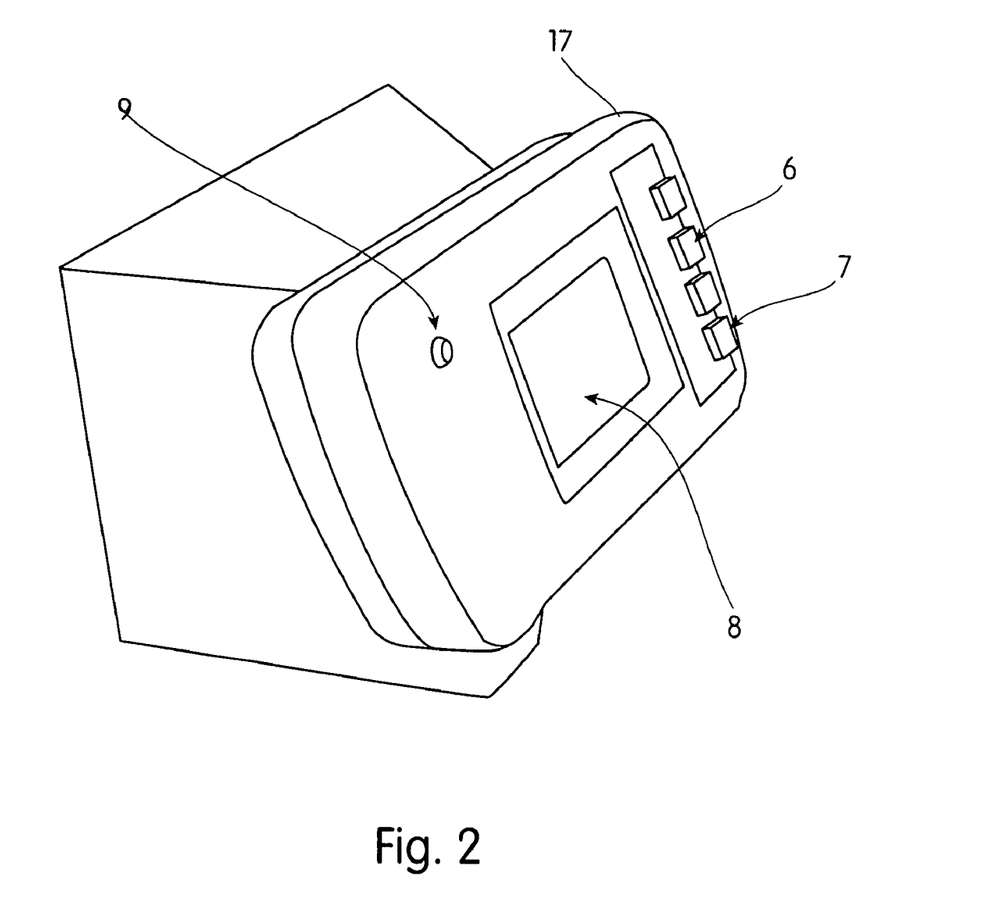
FIG. 2 is a perspective view of the radar of the present invention.

The present invention software operates on a standard Arm processor. The present invention is operated by pressing the On/Off buttons for at least one second. The on/off switch is the second 6 and fourth 7 buttons. The system requires thirty-five seconds before the LCD screen 8 lights up. In the meantime, the red LED in the upper left 9 flashes rapidly. Pressing the fourth button 7 again for more that five seconds turns the unit off.

Turning on the present invention initiates the radar. The radar is sensitive to extremely small motions and therefore requires one minute settling time for the integrators. Press the power button at will, but one can not reply on the results until the radar is fully settled. The radar is most sensitive to objects in front of the antenna within ±20° of centerline, however targets may be detected at any angle including behind the radar. The least sensitive position is directly behind the radar. When operated through a wall or other nearby obstacle, the beam may reflect backwards. Therefore, the best performance is obtained with a single operator directly behind the antenna. The more people that surround the antenna, the more extraneous signals may be present.

Figure 4:
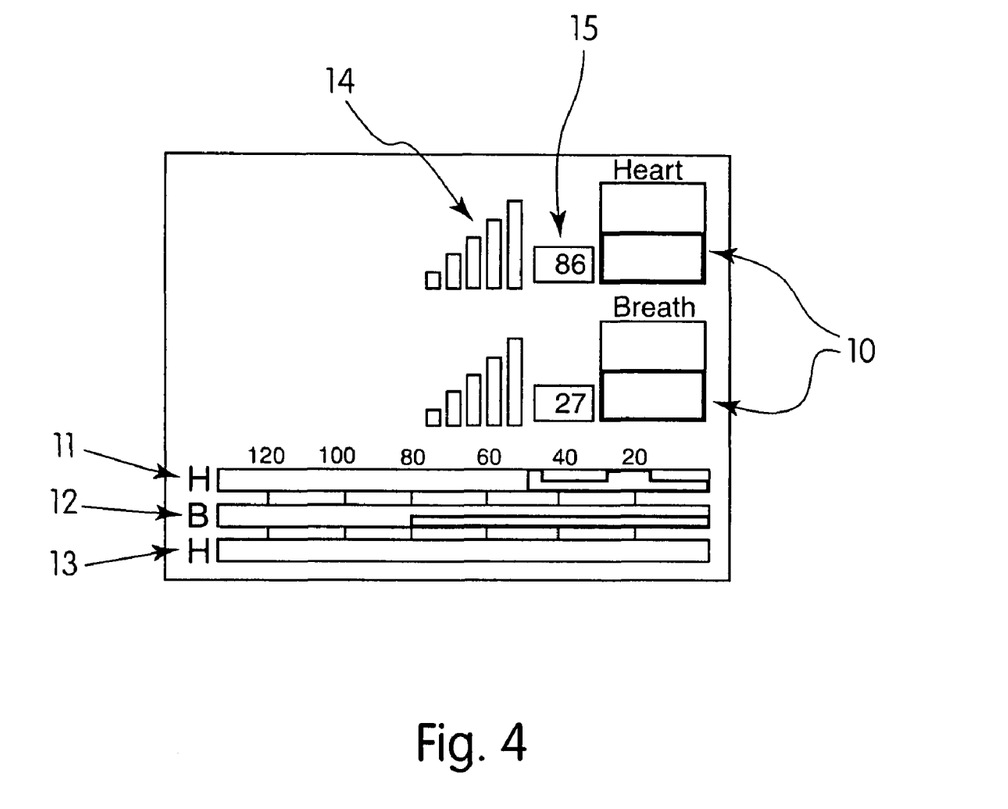
FIG. 4 is an example of a the display screen of the present invention.

The first indications of target detection are the large blue (or red) icons 10 in the upper right corner of the display 8. Red indicates target detection, blue indicates no-target detected. There is one icon for heart detection 11, motion 13, and one for breathing detection 12. There is also an indication of multiple targets. When a target is detected, the system tries to estimate a confidence number indicated by bars 14. Bars 14 go from zero to five bars.

If a target is detected, the system will present a rate 15. The rate 15 becomes more accurate over time and is correlated with confidence bars 14. When the indicator shows one or two targets, the lower bar(s) 11, 12, and 13 will turn red and track from right to left over one minute. This is to give a short history of target indication. Signals from the target are very small in the best of conditions, the system is making very close calls in many cases. The operator should use the one-minute history bars 11, 12, and 13 to improve his situational awareness and confidence.

To test the present invention the following simple calibration routine is used. First a user must ensure the present invention has batteries. Next, the most important part of operational status determination is a No Life Test. After waiting for settling, the present invention is placed in a typical operating position where no targets are present so that no moving objects within close proximity, approximately forty feet. If possible, the operator should step away. The operator may remain as close as 18" as long as he/she doesn't move significantly. Otherwise, three to ten feet may be necessary. The operator should wait sixteen seconds for the LCD 8 to indicate "No life detected." If the red indicator 9 is displayed, ensure the present invention is fully settled for two minutes and further ensure there are no nearby noise sources. A new data point is presented every second and data is used from the previous sixteen seconds to calculate target presence, confidence and rates.

For a life test, the present invention is placed with a living person in the detection zone. If testing through walls or foliage, they may be used in the test. The operator may remain close, but he/she shouldn't move significantly. Otherwise, three to ten feet may be helpful to ensure detection of the target vs detection of the operator. The operator should wait sixteen seconds for the red indicator 9 to indicate "Life detected." If a blue indicator is displayed, the operator should ensure the present invention is fully settled, which takes approximately two minutes. If the blue indicator continues, additional action must be taken to complete a successful test. The present invention is now operational and may be used to detect heartbeat and breathing.

Figure 3:
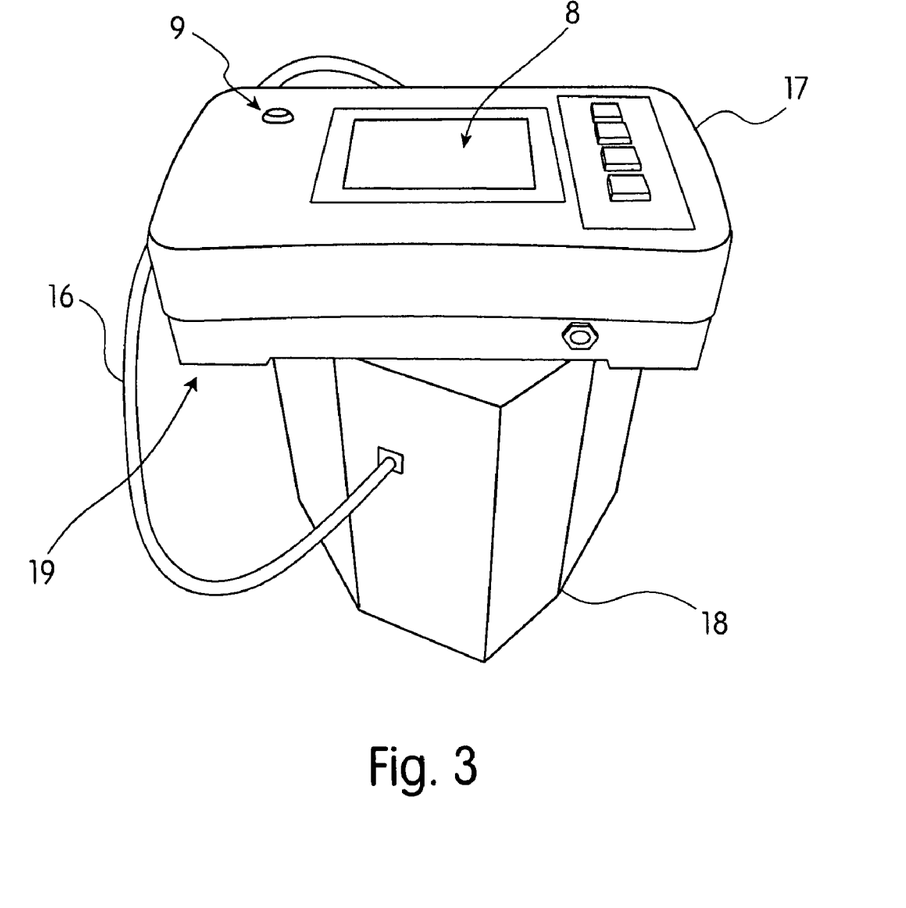
FIG. 3 is a perspective view of the radar mounted on a stable base.

Now referring to FIG. 3, the cable 16 connecting the radar 18 to the processor 17 is a standard 10-base-T Ethernet cable. It can be several feet long if it is desirable to operate the unit at a distance from the radar 18. The processor 17, uses four AA batteries 19. Four AA batteries 19 provide enough power for two Power-on/Reset and 2-4 hours of continuous run time. With external power during Power-on/Reset, the batteries will last six to eight hours. Approximately two hours of continuous use may be expected from new AA batteries 19.

FIG. 4 illustrates the radar 18 and its active face 21. The active face 21 of the radar 18 should be directed to the subject. The beam width of the radar 18 is approximately equivalent to that of the angle of the case.

An operator is now familiar with the operation of the present invention and is in a position to recognize noise issues. Any signals non-conforming to this initial set of measurements may be considered noise. It is incumbent on the operator to recognize and eliminate noise sources for proper operation.

There are several environmental factors that may effect the operation of the present invention. An operator that understands the basics of this section will obtain maximum performance from the present invention. Radar system performance depends largely on maximizing the signal while minimizing the noise. Signals are strictly determined by the radar power output convolved with the movement of the chest. Noise, on the other hand, is a function of many factors. Some potential noise sources are: undesired motion, fluorescent lighting, electronic noise, and rapid temperature variation.

Undesired motion such as operator motion or the motion of a nearby system (e.g. a computer fan). Moving objects will only be detected within the detection zone, typically forty feet maximum and may yield false Life indications.

Fluorescent lighting produces a strong motion signal to the radar (the plasma within the fluorescent light actually moves at 120 times per second) and may yield false Life indications. The radar is filtered to reduce the effect of fluorescent lights, but if the radar is pointed directly into a bank of lights, it is possible to cause false positives.

Electronic noise occurs when nearby electronics generates radio frequency noise that couples into the radar as a noise signal. This is the one case where the noise may be found outside the detection zone. For example, a cellular phone within three feet may interfere with the operation of the radar. Other radios may also interfere and depending on power output and frequency coupling, may interfere at greater distances from the sensor and may yield false Life indications. The radar operates in the 2.4 GHz band shared by many unlicensed devices such as wireless routers (802.11), Bluetooth and cordless telephones. See the calibration section to verify proper operation.

Rapid temperature variation occurs because the radar includes a very large gain amplifier stage and is sensitive to rapid temperature fluctuations and may yield false Life indications.

In all four cases, false Life indications are possible. In no case should a false No-Life indication be caused by noise. Great care has been taken to ensure that present invention errs on the side of false Life indication and that false No-Life indications are statistically as close to non-existent as possible.

All receivers have a noise floor, below which signals are too low to measure. This noise floor is primarily determined by the quality of the RF amplifier which is fairly standardized in today's IC's and the bandwidth of the received signal. The minimum heartbeat (rate and amplitude) and shallow breathing limits have not yet been tested.

Several features of the radar mitigate, but do not eliminate, noise signals. The first is a narrow filter that attenuates frequencies above five hertz by a factor of twelve dB per octave. This greatly reduces unwanted signals from fluorescent lighting as well as fans and other motor driven noise. It also somewhat reduces broadband electronic noise that may be modeled as Gaussian noise in the narrow (near baseband) passband of interest. The filter has a passband of 0.03 Hz to 5 Hz.

This passband was chosen because the fastest expected heartbeat should be 140 beats per minute (bpm) and the slowest breathing could be a few breaths per minute. The 0.03 to 5 Hz passband covers these extremes with a margin of safety. The narrow passband also optimizes receiver noise to its lowest level.

A brief description of frequency (Fourier) analysis is in order for those who delve into the details of the output signal. If one were to match an ECG or EKG signal to a radar output signal, there would be a very good correlation. By limiting the frequency of this radar to five hertz, only the first few components of the desired (heartbeat) signal are presented. This signal will match the heart rate in beats per minute.

The second key feature is the range gate of the radar. Motion sources outside the range gate are attenuated.

Signal processing is also utilized to mitigate noise as described below. Once the signal is converted to digital, the software processes the results as follows.

A Fourier analysis is performed to convert the time series into a frequency representation. It's still the same signal, simply broken down into its frequency components. By this method the breathing and heart rate signal show-up in their respective frequency "bins." On the second heartbeat, the signal within the heartbeat bin doubles coherently while the noise adds incoherently. The expected heart rate bins may then be compared to noise bins and a threshold set. The longer the measurement, the more accurate the result, however a decision is presented in sixteen seconds as required.

The present invention comes pre-loaded with all the software necessary to operate. The present invention has no user-serviceable parts. Reloading the software should never be necessary. The firmware is permanently programmed.

TABLE 1

The Specifications and Typical Performance of the Present Invention

| Specifications | Typical Performance |
| --- | --- |
| Sensitivity | 1.2 mV/cm² @ 1 Hz |
| Doppler Passband | 0.03-5 Hz |
| Dynamic Range | 95 dB |
| Noise | 4 µV |
| Voltage (PDA batt.) | 3.6 V |
| Current | 900 mA |
| Size, Weight | 14" × 14" × 8, 32 oz. |
| Temp | −10° to +60° C. |

To reduce the vibration caused by human interface during the operation of the hand-held radar that Inventor is developing will use piezoelectric actuators to create an out of phase signal that will combine with the baseline signal. During normal operating conditions the largest disturbances of the measurement system are introduced by the low frequency hand swinging motion, by the human hearth beat. Such radar needs to be stable in all six axes for long periods of time (up to ninety seconds). Inventor proposes to use an active control system based upon piezoelectric actuators and sensors. The piezoelectric actuators will generate an out of phase signal that will combine with the baseline signal. The combined signal will be considerably more stable than the baseline.

The system will be controlled in each of its axes. In this case the actuators and sensors will work with the custom control electronics developed for this case. The goal of the control theory will be to minimize the error at the performance measurement. Selection of the sensor and actuator will depend upon the details of the structure that comprises the radar.

Inventor will select the appropriate sensors and actuators in order to minimize the cost of the system and maximize the performance. It is expected that either bender or stack type actuators may be used. Similar type electronics can be built to address the motion control of the radar system. Piezo Control Circuitry includes: Multi-layer Actuator; Speaker-type Actuator; Energy Harvesting; Stack-type; Bender-type; Custom; and Raw Piezo Fibers.

Figure 5:
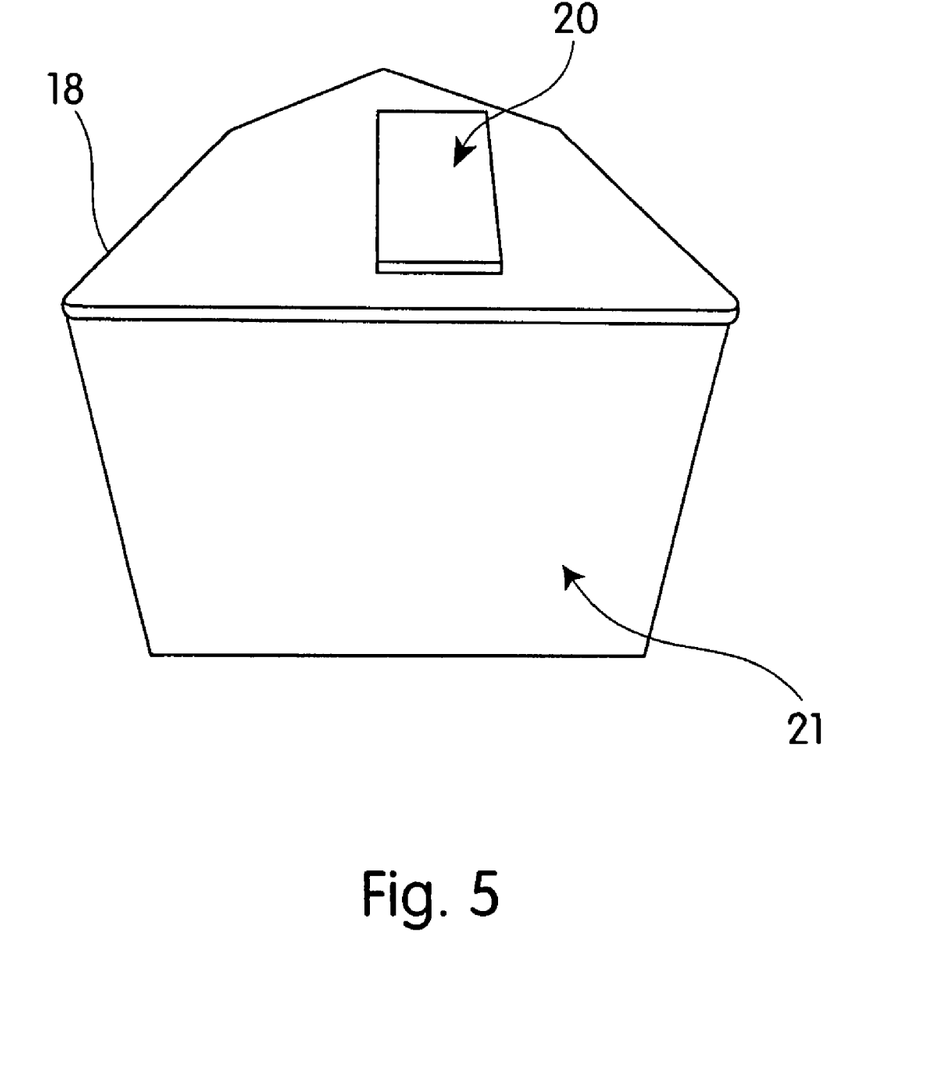
FIG. 5 is the radar's active face.

It is expected that with an active control system a significant vibration reduction can be achieved. Such reduction will lead too much greater radar position accuracy. A 1 micron accuracy can be achieved with the combination of axes of control. FIG. 5 shows a typical result for an aerospace example. In this case a 20 dB reduction was obtained in the first two vibration modes using an LQG (Linear Quadratic Gaussian) control algorithm.

The scope of the present invention is to prove feasibility of the concept by demonstrating the functionality of an active stabilization system. In order to achieve that goal, the program is divided into two phases and a total of seven tasks as highlighted below.

Inventor's engineers have analyzed the Radar Cross Section (RCS) of heart and breathing targets. As the radar return signal from breathing or heartbeat is weaker than the signal from a motion detector of a larger object, the link budget and sensitivity of the low power radar must be accurately determined. Hence, the Radar Cross Section (RCS) measurement data and antenna calibration are important components of this analysis. The RCS is formally defined by the ratio of incident and scattered field strengths, and depends on the characteristics size, shape, and constitutive material, spatial configuration, aspect angle, polarization, and frequency. The calibration of antennas and measurement of RCS are performed routinely by Inventor design engineers. The sequence of steps described below can be used to produce all RCS calculations.

In order to determine the RCS, consider for the moment a bi-static radar equation (while we use a mono-static radar, the bi-static method described can be used to approximate RCS determination if the receiver and transmitter antennas are closely located). The bi-static radar equation may be written as:

$$\frac{P_r}{P_t} = G_t \frac{1}{4\pi R_t^2} \sigma \frac{1}{4\pi R_r^2} \frac{G_r \lambda^2}{4\pi} \quad \text{Equation 1}$$

Equation (1), above represents the ratio of received to transmitted power when the signal is reflected off an object with RCS. In equation (1), G represents the transmitting and receiving antenna gains, and R the ranges from the transmitter and receiver to the target. If we point the antennas toward each other with separation, there is no reflection and only one geometric loss term. Calculating the minimum detectable signal level:

The signal level may be estimated from the level above the noise floor. The noise floor may be derived from equation (2) below:

$$V_{noise} = \sqrt{z \cdot P_{noise}} = \sqrt{50 \cdot kTB_w} = -55 \text{ dB}V = 3 \text{ µV} \quad \text{Equation 2}$$

To measure the platform motion signal a rate table at Eglin AF Base's Guided Weapons Evaluation Facility (GWEF) was utilized.

The 46th Test Wing is responsible for the test and evaluation (T&E) of non-nuclear munitions, electronic countermeasures, and navigation/guidance systems for the Air Armament Center. The Wing performs the research, development, test and evaluation (RDT&E) of systems for US and international governments, the DoD and other federal and state government agencies, and private industry. The Wing also operates, maintains and manages the Eglin AFB land and water ranges, a complex exceeding 120,000 square miles.

From the data it can be seen that an extrapolation may be made to the minimum detectable signal level of the radar. This is the point where the radar must provide more target signal than platform signal in order for the computer to recognize valid heart and breathing signals. Therefore, a minimum motion may be derived in each degree of freedom follows.

Platform motion has been measured vs. radar signal output in a typical (lab) environment. The signal level was extrapolated to the minimum detectable signal and the minimum acceptable platform motion derived. In general, the platform must be stabilized to one micron.

It is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention. Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A radar detection system consisting of:
   a MPR ultra-wideband (UWB) radar;
   the radar consists of radar UWB transmitter and UWB receiver implemented by several circuit boards mounted in a stack;
      a data acquisition element implemented by two circuit boards in a stack;
      the data acquisition element implemented by a processor consisting of two circuit boards in a stack;
   a display implemented by a PDA;
   a power supply;
   transmitting a sequence of pulses with a 2.4 GHz bandwidth;
   receiving one ore more of the sequence of transmitted pulses; and
   independently measuring a life rate induced Doppler shift and a range to a hidden source of this life rate for each pulse received and measured.

2. The radar detection device of claim 1 wherein, the radar sends a ultra wideband signal of radio frequency energy toward the target scene; the signal reflects from the target scene and is received as a Doppler change.

3. The radar detection device of claim 2 wherein, the radar detects human a heartbeat and breathing at a forty-foot range.

4. The radar detection device of claim 1 wherein, the radar is mounted on a stationary platform.

5. The radar detection device of claim 4 wherein, the stationary platform is a tripod.

6. The radar detection device of claim 4 wherein, the radar is integrated with a gyroscopically stabilized platform providing directing the radar at a person to determine a live or dead condition and register pulse and respiration rates.

7. The radar detection device of claim 6 further comprising:
   integrating the MPR ultra-wideband (UWB) radar, data acquisition element, processor, and software into a manufacturable handheld package;
   the processor and the software detecting an operator's heart and breathing signal on a second channel and subtracting it;
   the processor and the software filtering clutter artifacts and compensating for the clutter artifacts through algorithm developments;
   a mechanical feedback control to hold the antenna steady compensating for micro-motion in the operator's hand;
   accelerometers providing operator stability feedback; and
   the processor and the software processing detected physiologic and biometric phenomena.

8. The radar detection device of claim 6 further comprising:
   a monopulse antenna, sum and difference circuitry, acquisition element, processing, and processing software providing side-to-side, azimuthal, target resolution and
   networking, data basing, and up linking connected to an external casualty tracker system.

9. The radar detection device of claim 1 wherein,
   a Doppler change in signal amplitude is filtered, amplified and presented to the data acquisition means;
   data acquisition means converts the analog Doppler signal into a digital bit-stream and passed the signal to the processor; and
   software analysis filters the signal to make a Live/Dead determination.

10. The radar detection device of claim 1 wherein,
    a radar antenna is located at the back of the device; and
    the antenna should be pointed toward the victim or test subject, the display facing the operator.

11. The radar detection device of claim 1 wherein,
    the radar is a pulse Doppler design with moving target indicator and sensitivity time control;
    the radar thereby creates a zone or bubble of detection;
    any motion within the bubble results in an analog signal reported at the output of the radar;
    the system collects radar signal information and signal processing is used to calculate target parameters; and
    a new data point is presented every second and data is used from the previous sixteen seconds to calculate target presence, confidence and rates.

12. The radar detection device of claim 1 further comprising a low noise receiver for sensitive detection of heartbeat and breathing rates of less than 1 microvolt and multi-target detection.

13. The radar detection device of claim 1 wherein, targets are detected at any angle surrounding the radar.

14. The radar detection device of claim 1 wherein, the radar is most sensitive to objects in front of the antenna within 20 degrees to each side of the centerline.

15. The radar detection device of claim 1 wherein,
    there is one icon each for heart detection, motion, and breathing detection;
    there is an indication of multiple targets;
    when a target is detected, the system tries to estimate a confidence number.

16. The radar detection device of claim 1 wherein, the confidence number indicated by zero to five bars.

17. The radar detection device of claim 15 wherein, the rate becomes more accurate over time and is correlated with confidence bars.

18. The radar detection device of claim 1 wherein, when an indicator shows one or two targets, the bar will turn red and track from right to left over a one minute period to give a short history of target indication.

19. The radar detection device of claim 1 further comprising:
- a narrow filter that attenuates frequencies above five hertz by a factor of twelve dB per octave having a passband of 0.03 Hz to 5 Hz;
- a range gate of the radar providing attenuation for motion sources outside the range gate; and
- signal processing mitigating noise using a Fourier analysis to convert the time series into a frequency representation.

20. The radar detection device of claim 1 further comprising:
- piezoelectric actuators and sensors to create an out of phase signal that will combine with the baseline signal;
- the combined signal will be considerably more stable than the baseline;
- the system is controlled in each of its axes; and
- the actuators and sensors provide means to minimize the error at the performance measurement.

* * * * *